United States Patent
Ashcroft et al.

(10) Patent No.: US 9,220,665 B2
(45) Date of Patent: Dec. 29, 2015

(54) ORAL CARE COMPOSITIONS

(75) Inventors: Alexander Thomas Ashcroft, Wirral (GB); Jian Cao, Shanghai (CN); Shouwei Ma, Shanghai (CN); Edward George Pelan, Vlaardingen (NL); Simeon Dobrev Stoyanov, Vlaardingen (NL); Weizheng Zhou, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/345,013

(22) PCT Filed: Sep. 12, 2012

(86) PCT No.: PCT/EP2012/067785
§ 371 (c)(1),
(2), (4) Date: Sep. 15, 2014

(87) PCT Pub. No.: WO2013/041419
PCT Pub. Date: Mar. 28, 2013

(65) Prior Publication Data
US 2015/0050322 A1     Feb. 19, 2015

(30) Foreign Application Priority Data
Sep. 23, 2011   (WO) ................ PCT/CN2011/001607

(51) Int. Cl.
*A61K 8/19*       (2006.01)
*A61Q 11/00*      (2006.01)
(Continued)

(52) U.S. Cl.
CPC ............... *A61K 8/0245* (2013.01); *A61K 8/027* (2013.01); *A61K 8/19* (2013.01); *A61K 8/345* (2013.01); *A61Q 11/00* (2013.01); *A61K 2800/28* (2013.01); *A61K 2800/412* (2013.01)

(58) Field of Classification Search
CPC ................... A61K 2800/28; A61K 2800/412; A61K 8/0245; A61K 8/027; A61K 8/19; A61K 8/345; A61Q 11/00
See application file for complete search history.

(56) References Cited

U.S. PATENT DOCUMENTS 4,743,274 A   5/1988   Ozawa et al.
6,022,517 A   2/2000   Fairchild et al.
(Continued)

FOREIGN PATENT DOCUMENTS

CN   1310995 A    9/2001
EP   406662 A1    1/1991
(Continued)

OTHER PUBLICATIONS

Pickles M J et al., In vitro efficacy of a whitening toothpaste containing calcium carbonate andperlite, International Dental Journal Butterworth and Co Ltd GB, Jan. 1, 2005, 197-202. vol. 55 No. 3 Suppl 1, GB.

(Continued)

*Primary Examiner* — Ernst V Arnold
(74) *Attorney, Agent, or Firm* — Greenberg Traurig, LLP

(57) ABSTRACT

The invention provides an oral care composition comprising: (a) a continuous phase comprising water or polyhydric alcohol or a mixture thereof; and (b) a particulate calcium carbonate abrasive composed of primary particles which are acicular and which have a length of 2 microns or greater; in which the level of the particulate calcium carbonate abrasive ranges from 10 to 70%, preferably from 20 to 60%, more preferably from 30 to 40%, by total weight of the particulate calcium carbonate abrasive based on the total weight of the composition. The composition of the invention demonstrates satisfactory levels of cleaning, yet is not unduly abrasive and damaging to the teeth.

8 Claims, 1 Drawing Sheet

Figure 1A:
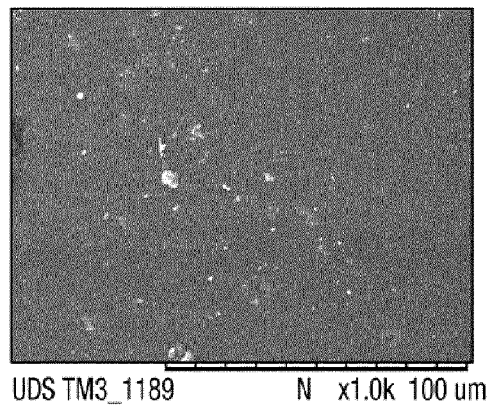

(51) Int. Cl.
   *A61K 8/02* (2006.01)
   *A61K 8/34* (2006.01)

(56) References Cited

U.S. PATENT DOCUMENTS

| | | | |
|---|---|---|---|
| 6,071,336 A * | 6/2000 | Fairchild et al. | 106/464 |
| 6,808,700 B2 | 10/2004 | Kiji et al. | |
| 2004/0161388 A1 | 8/2004 | Liu | |
| 2006/0275224 A1* | 12/2006 | Burnet et al. | 424/52 |
| 2008/0220148 A1 | 9/2008 | Clarkson et al. | |
| 2009/0130150 A1 | 5/2009 | Gazzaniga et al. | |
| 2010/0015068 A1* | 1/2010 | Karp et al. | 424/57 |
| 2010/0135891 A1 | 6/2010 | Hansen et al. | |

FOREIGN PATENT DOCUMENTS

| WO | WO0010520 | 3/2000 |
|---|---|---|
| WO | WO2004105680 | 12/2004 |
| WO | WO2006050365 | 5/2006 |
| WO | WO2007078016 A1 | 7/2007 |
| WO | WO2009134657 A1 | 11/2009 |

OTHER PUBLICATIONS

International Search Report, PCT/CN2011/001607 mailed Jul. 5, 2012, 5 pp.
International Search Report, PCT/EP2012/067785, mailed Feb. 18, 2013, 4 pp.
IPRP2 in PCTEP2012067785, Jul. 16, 2013.
Written Opinion in PCTCN2011001607, Jul. 5, 2012.
Written Opinion in PCTEP2012067785, Feb. 18, 2013.
Alan Rawle, The importtance of particle sizing to the chaotings industry Part 1: Particle size measurement, Advances in Colour Science and Technology, Jan. 2002, pp. 1-5, vol. 5, No. 1, May 4, 2015.

* cited by examiner

ORAL CARE COMPOSITIONS

FIELD OF THE INVENTION

The present invention is concerned with oral care compositions. More particularly, the present invention is concerned with oral care compositions containing calcium carbonate as an abrasive, and having low abrasivity whilst maintaining desirable cleaning properties.

BACKGROUND OF THE INVENTION

Abrasives for use in oral care compositions such as dentifrices, are required to be effective in removing extrinsic stains, dental plaque and food debris which builds up on the pellicle on the surface of teeth.

In general, the efficiency of physical removal of stain, plaque and food debris can be increased by using an abrasive having increased abrasivity. However, increasing abrasivity also increases the risk that tooth surfaces may be damaged.

Accordingly, there is a continuing need for oral care compositions that demonstrate satisfactory levels of cleaning, yet are not unduly abrasive and damaging to the teeth.

The present inventors have found that this problem can be solved by the use of a calcium carbonate abrasive having a particular particle size and shape.

U.S. Pat. No. 4,743,274 relates to the modification of crystal morphology to provide a high cleaning, low abrading abrasive for use in oral compositions. This describes how, in the case of an abrasive which consists of calcium hydrogenphosphate anhydride (secondary calcium phosphate anhydride), reducing the average crystallite size produces a material which meets both the requirements of high tooth cleanability and low tooth surface abrasiveness.

US2004/0161388 mentions how the dentifrice-relevant properties of a calcium carbonate material are correlated to its morphology and particle size, and describes how small scalenohedral-shaped calcium carbonate particles tend to have relatively insignificant cleaning effectiveness, whereas large rhombohedral-shaped (sometimes referred to as "cubic") calcium carbonate particles have increased cleaning and abrasive benefits, but often abrade too well: their abrasiveness leading to a concern for possible damage to teeth and gums. As a solution to this problem, US2004/0161388 proposes an abrasive, precipitated calcium carbonate having a primary particle size of about 1 to 4 microns. These primary particles themselves may come together and, through covalent bonding to one another, form aggregates having a particle size of about 3 to 10 microns. The material has a calcite crystalline form and essentially a cubic crystal structure.

SUMMARY OF THE INVENTION

The present invention provides an oral care composition comprising:
(a) a continuous phase comprising water or polyhydric alcohol or a mixture thereof; and
(b) a particulate calcium carbonate abrasive composed of primary particles which are acicular and which have a length of 2 microns or greater;
in which the level of the particulate calcium carbonate abrasive ranges from 10 to 70%, preferably from 20 to 60%, more preferably from 30 to 40%, by total weight of the particulate calcium carbonate abrasive based on the total weight of the composition.

DETAILED DESCRIPTION OF THE INVENTION

Particulate Calcium Carbonate Abrasive

The composition of the invention comprises, inter alia, a particulate calcium carbonate abrasive composed of primary particles which have a specific shape and size, as defined above.

By "primary particles" is meant individual particles. For the purposes of the present invention, the primary particles of the particulate calcium carbonate abrasive are acicular and have a length of 2 microns or greater.

The primary particles may associate under certain conditions to form larger secondary structures such as aggregates or agglomerates.

If desired, the primary particles may be surface-modified, for example by coating with hydrophobic materials such as ethylcellulose, hydroxypropylcellulose, waxes (such as shellac, carnauba or beeswax) and fat or fatty acids such as stearic and oleic acid. Coating can be done using colloidal precipitation using solvent or temperature change, for instance.

For the purposes of the present invention, a suitable class of particulate calcium carbonate abrasive includes crystalline calcium carbonates in which the crystals are acicular and have a length of 2 microns or greater.

The term "crystal" means an essentially fully dense solid composed of atoms arranged in an orderly repetitive array bounded by plane surfaces which are the external expression of internal structure.

Calcium carbonate may occur naturally or may be synthetically produced in three particular crystalline morphologies, calcite, aragonite, and less commonly found, vaterite. The vaterite form of calcium carbonate is metastable and irreversibly transforms into calcite and aragonite. There are many different polymorphs (crystal habits) for each of these crystalline forms. The calcite crystalline morphology is the most commonly used crystal form of calcium carbonate. Over 300 crystalline forms of calcite have been reported in the literature.

The term "acicular" in this context refers to the shape of the crystals. Usually, crystals grow in three directions, length, width and height. Some crystals however, have one or two preferred growth directions. Acicular crystals have a preferred crystal growth in one direction. Examples are crystals in the form of needles, rods, fibres, whiskers or columns and the like. For the purposes of the present invention, preferred acicular crystals are rod-like or needle-like with a generally uniform, typically generally circular, cross-sectional shape.

The ratio between the length and the width of a crystal, the so-called aspect ratio, is higher than 1:1 for acicular crystals. The higher the aspect ratio, the longer the crystal. For the purposes of the present invention the aspect ratio is preferably at least 2.5:1, more preferably at least 10:1. For example the aspect ratio may typically range from 2.5:1 to 200:1, and preferably ranges from 10:1 to 60:1, more preferably from 20:1 to 30:1.

Acicular crystalline forms of calcium carbonate are available naturally, or may be produced by precipitation production technology. Typically, precipitated calcium carbonate is prepared by exposing calcium hydroxide slurry to a carbonation reaction.

Preferred acicular calcium carbonate crystals for use in the invention have a length ranging from 2 to 100 microns, more preferably from 10 to 30 microns and a width ranging from 0.1 to 4.0 microns, more preferably from 0.5 to 1.0 microns.

Crystal morphology and structure may be determined by standard techniques known to those skilled in the art such as scanning electron microscopy (SEM). SEM is an imaging and analysis technique based on the detection of electrons and X-rays that are emitted from a material when irradiated by a scanning electron beam. Imaging allows the user to distinguish between primary particle and agglomerate sizes.

Automated image analysis using computer software enables the user to determine particle size distributions. Scanning electron microscopy (SEM) is a particle counting technique and produces a number-weighted size distribution. Accordingly the figures quoted herein for particle length and width will generally represent average values over a population of particles, more specifically the D[1,0] number-length mean of the particle length or the particle width respectively.

A specific class of material suitable for use in the invention includes aragonite crystal form calcium carbonates such as those described for example in U.S. Pat. No. 5,164,172. According to U.S. Pat. No. 5,164,172, aragonite crystal form calcium carbonate with an acicular shape is prepared by pre-mixing aragonite calcium carbonate and $Ca(OH)_2$ to prepare an aqueous slurry, adding a water-soluble phosphoric acid compound (such as phosphoric acid or a water-soluble salt thereof) into the aqueous slurry, and introducing $CO_2$ gas into the aqueous slurry to cause a carbonation reaction to take place. In this process, the molar ratio of the aragonite calcium carbonate to $Ca(OH)_2$ slurry is preferably 1:7 to 1:5000. The resulting aragonite calcium carbonate crystals have an acicular shape and have a particle size of 10 to 100 microns (length) by 0.5 to 4.0 microns (width). The exemplified crystals are shown by microscopy to be rod-like or needle-like with a length of 10 to 100 microns. The rods or needles are generally uniform and typically circular in cross-section, with a cross-sectional diameter of 0.5 to 4.0 microns. For the purposes of the present invention, the most preferred aragonite calcium carbonate crystals are rod-like or needle-like as described above, with a length ranging from 10 to 30 microns, a width ranging from 0.5 to 1.0 microns and an aspect ratio ranging from 20:1 to 30:1.

Suitable aragonite crystal form calcium carbonates for use in the invention are commercially available and include those marketed by Maruo Calcium Company Limited, Japan under the trade name WHISCAL®.

Mixtures of any of the above described materials may also be used.

The level of particulate calcium carbonate abrasive (as defined above) generally ranges from 10 to 70%, preferably from 20 to 60%, more preferably from 30 to 40%, by total weight particulate calcium carbonate abrasive (as defined above) based on the total weight of the composition.

The oral care compositions of the invention demonstrate satisfactory levels of cleaning, yet are not unduly abrasive and damaging to the teeth. A further advantage of the oral care compositions of the invention is that they are gentle enough for use on bridgework, dentures and other forms of artificial teeth which are made from polymers much softer than natural tooth enamel, such as acrylic resin (PMMA).

The level of cleaning ability of the composition of the invention may be measured by assessing its effect on accumulated pellicle, for example by using a method such as that described by Pickles et al. (*International Dental Journal* 55 (2005), pp. 197-202). This model uses enamel slabs cut from bovine central incisors, embedded in methacrylate resin. The enamel surfaces are smoothed by hand using an alumina paste on a glass block and lightly acid etched in order to facilitate stain accumulation and adherence. The enamel blocks are placed in an incubator set at a constant temperature of 50° C. and slowly rotated to alternate between immersion in a staining broth (consisting of tea, coffee and mucin) and air drying. The broth is changed daily and after five days the slabs are removed and washed with distilled water to remove any loose debris. The stained slabs are then brushed in a mechanical brushing machine with distilled water to remove any loosely adhered stain. They are then dried and the L* values ($L^*_{stained}$) from the CIE L*a*b* colour system are measured with a chroma meter in L*a*b* mode. To assess cleaning performance, the stained specimens are then mounted in the mechanical brushing machine and the required load applied to each brush. The test composition is dispersed in an aqueous diluent to form a slurry (typically 38.5 g test composition and 61.5 g of distilled water) and the stained specimens brushed for a set number of brush strokes with 10 ml of slurry. After brushing, the enamel slabs are rinsed with distilled water, dried and the L* values ($L^*_{brushed}$) are re-measured. In the final stage, all traces of stain are removed from the enamel slabs using flour of pumice, on a soft cloth using a grinder/polisher. The enamel slabs are then rinsed with distilled water, dried and the L* values ($L^*_{pumiced}$) are measured and recorded. The percentage of the stain removed by the test composition compared to full removal by pumice (hereinafter referred to as the pellicle cleaning ratio or PCR) may be calculated using the following equation:

$$PCR=[(L^*_{brushed})-(L^*_{stained})/(L^*_{pumiced})-(L^*_{stained})]\times 100$$

The composition of the invention preferably has a PCR value of at least 30%, more preferably at least 40%, most preferably at least 45%.

The level of abrasivity of the composition of the invention may be assessing its Radioactive Dentine Abrasion Test (RDA) value. A standard test procedure for measuring these values follows the method for assessment of dentifrice abrasivity recommended by the American Dental Association (Journal of Dental Research 55(4) 563, 1976). In this procedure, extracted human teeth are irradiated with a neutron flux and subjected to a standard brushing regime. The radioactive phosphorus 32 removed from the dentin in the roots is used as the index of the abrasion of the composition tested. A reference slurry containing 10 g of calcium pyrophosphate in 50 $cm^3$ of 0.5% aqueous solution of sodium carboxymethyl cellulose is also measured and the RDA of this mixture is arbitrarily taken as 100. In order to measure the RDA for the test composition, a slurry of 25 g of the test composition in 40 $cm^3$ water is prepared and submitted to the same brushing regime.

The composition of the invention preferably has a RDA value of no more than 100, more preferably no more than 80, most preferably no more than 60.

The composition of the invention preferably has a PCR: RDA ratio of at least 0.5, more preferably at least 0.6, most preferably at least 0.8.

Product Form

A preferred type of product form in the context of the present invention is a dentifrice. The term "dentifrice" denotes a formulation which are used to clean the surfaces of the oral cavity. The dentifrice is an oral composition that is not intentionally swallowed for purposes of systemic administration of therapeutic agents, but is retained in the oral cavity for a sufficient time to contact substantially all of the dental surfaces and/or mucosal tissues for purposes of oral activity. Preferably the dentifrice is suitable for application with a toothbrush and is rinsed off after use. Preferably the dentifrice is in the form of an extrudable semi-solid such as a cream, paste or gel (or mixture thereof).

A dentifrice composition according to the invention will usually contain a liquid continuous phase in an amount of from 40 to 99% by weight based on the total weight of the dentifrice. Such a liquid continuous phase will typically comprise a mixture of water and polyhydric alcohol in various relative amounts, with the amount of water generally ranging from 10 to 45% by weight (based on the total weight of the dentifrice) and the amount of polyhydric alcohol generally ranging from 30 to 70% by weight (based on the total weight of the dentifrice). Typical polyhydric alcohols include humectants such as glycerol, sorbitol, polyethylene glycol, polypropylene glycol, propylene glycol, xylitol (and other edible polyhydric alcohols), hydrogenated partially hydrolyzed polysaccharides and mixtures thereof.

A dentifrice composition according to the invention will generally contain further ingredients to enhance performance and/or consumer acceptability.

For example, the dentifrice may comprise other abrasive materials (in addition to the particulate calcium carbonate abrasives described above). Such other abrasive materials will generally be present in an amount of from 3 to 75% by weight based on the total weight of the dentifrice. Suitable other abrasive materials include abrasive silicas, other calcium carbonates (which are different to the particulate calcium carbonate abrasives described above), dicalcium phosphate, tricalcium phosphate, calcined alumina, sodium and potassium metaphosphate, sodium and potassium pyrophosphates, sodium trimetaphosphate, sodium hexametaphosphate, particulate hydroxyapatite and mixtures thereof.

Furthermore, the dentifrice will usually contain a binder or thickening agent in an amount of from 0.5 to 10% by weight based on the total weight of the dentifrice. Suitable binders or thickening agents include carboxyvinyl polymers (such as polyacrylic acids cross-linked with polyallyl sucrose or polyallyl pentaerythritol), hydroxyethyl cellulose, hydroxypropyl cellulose, water soluble salts of cellulose ethers (such as sodium carboxymethyl cellulose and sodium carboxymethyl hydroxyethyl cellulose), natural gums (such as carrageenan, gum karaya, guar gum, xanthan gum, gum arabic, and gum tragacanth), finely divided silicas, hectorites, colloidal magnesium aluminium silicates and mixtures thereof.

Furthermore, the dentifrice will usually contain a surfactant in an amount of from 0.2 to 5% by weight based on the total weight of the dentifrice. Suitable surfactants include anionic surfactants, such as the sodium, magnesium, ammonium or ethanolamine salts of $C_8$ to $C_{18}$ alkyl sulphates (for example sodium lauryl sulphate), $C_8$ to $C_{18}$ alkyl sulphosuccinates (for example dioctyl sodium sulphosuccinate), $C_8$ to $C_{18}$ alkyl sulphoacetates (such as sodium lauryl sulphoacetate), $C_8$ to $C_{18}$ alkyl sarcosinates (such as sodium lauryl sarcosinate), $C_8$ to $C_{18}$ alkyl phosphates (which can optionally comprise up to 10 ethylene oxide and/or propylene oxide units) and sulphated monoglycerides. Other suitable surfactants include nonionic surfactants, such as optionally polyethoxylated fatty acid sorbitan esters, ethoxylated fatty acids, esters of polyethylene glycol, ethoxylates of fatty acid monoglycerides and diglycerides, and ethylene oxide/propylene oxide block polymers. Other suitable surfactants include amphoteric surfactants, such as betaines or sulphobetaines. Mixtures of any of the above described materials may also be used.

Compositions of the present invention (such as in particular dentifrices) may also contain further optional ingredients customary in the art such as fluoride ion sources, anticalculus agents, buffers, flavouring agents, sweetening agents, colouring agents, opacifying agents, preservatives, antisensitivity agents and antimicrobial agents.

The invention is further illustrated with reference to the following, non-limiting Examples.

EXAMPLES

Example 1 and Comparative Examples A to G

Eight oral care formulations were prepared, incorporating a range of different particulate calcium carbonate abrasives. The ingredients of the formulations are shown in Tables 1 and 2 below. Example 1 represents a formulation according to the invention. The remaining formulations are comparative examples (not according to the invention).

TABLE 1

| Ingredient | Example 1 | Comp.Ex. A | Comp.Ex. B | Comp. Ex. C |
|---|---|---|---|---|
| Water | to 100 | to 100 | to 100 | to 100 |
| Sorbitol | 21 | 21 | 21 | 21 |
| Thickening silica | 2.4 | 2.4 | 2.4 | 2.4 |
| Sodium lauryl sulphate | 1.6 | 1.6 | 1.6 | 1.6 |
| Flavour | 1.2 | 1.2 | 1.2 | 1.2 |
| Sodium monofluorophosphate | 1.09 | 1.09 | 1.09 | 1.09 |
| Trisodium phosphate | 1.07 | 1.07 | 1.07 | 1.07 |
| Titanium dioxide (anatase) | 1 | 1 | 1 | 1 |
| Sodium carboxymethyl cellulose | 0.7 | 0.7 | 0.7 | 0.7 |
| Sodium saccharin | 0.27 | 0.27 | 0.27 | 0.27 |
| Methyl paraben | 0.15 | 0.15 | 0.15 | 0.15 |
| Propyl paraben | 0.05 | 0.05 | 0.05 | 0.05 |
| Calcium carbonate rods[1] | 40 | — | — | — |
| STURCAL ® F[2] | — | 40 | — | — |
| OMYACARB ® 5-AV[3] | — | — | 40 | — |
| VICRON ® Food Grade 45-3[4] | — | — | — | 40 |

[1]Precipitated calcium carbonate ex Maruo Calcium Company Limited, consisting of aragonite rods/needles with length 10 to 30 microns and diameter 0.5 to 1.0 micron.
[2]Precipitated calcium carbonate ex Speciality Minerals Inc., consisting of agglomerates of acicular aragonite crystals, crystal length about 1 micron or less. The agglomerates have an average particle size (d50) of about 2.5 micron (equivalent spherical diameter).
[3]Ground calcium carbonate ex Omya, which is fine ground natural marble from Avenza, Italy, having an irregular rhombohedral particle shape and a median particle diameter of 5 μm.
[4]Ground calcium carbonate ex Speciality Minerals Inc., which is fine ground natural limestone from Adams, MA, with an irregular rhombohedral particle shape and an average particle size of 10.0 microns.

TABLE 2

| Ingredient | Comp.Ex. D | Comp.Ex. E | Comp.Ex. F | Comp. Ex. G |
|---|---|---|---|---|
| Water | to 100 | to 100 | to 100 | to 100 |
| Sorbitol | 21 | 21 | 21 | 21 |
| Thickening silica | 2.4 | 2.4 | 2.4 | 2.4 |
| Sodium lauryl sulphate | 1.6 | 1.6 | 1.6 | 1.6 |
| Flavour | 1.2 | 1.2 | 1.2 | 1.2 |
| Sodium monofluorophosphate | 1.09 | 1.09 | 1.09 | 1.09 |
| Trisodium phosphate | 1.07 | 1.07 | 1.07 | 1.07 |
| Titanium dioxide (anatase) | 1 | 1 | 1 | 1 |
| Sodium carboxymethyl cellulose | 0.7 | 0.7 | 0.7 | 0.7 |
| Sodium saccharin | 0.27 | 0.27 | 0.27 | 0.27 |
| Methyl paraben | 0.15 | 0.15 | 0.15 | 0.15 |
| Propyl paraben | 0.05 | 0.05 | 0.05 | 0.05 |
| ViCALity ® Extra Heavy[5] | 40 | — | — | — |
| ViCALity ® GF4[6] | — | 40 | — | — |

TABLE 2-continued

| Ingredient | Comp.Ex. D | Comp.Ex. E | Comp.Ex. F | Comp. Ex. G |
|---|---|---|---|---|
| CalEssence ® 450 [7] | — | — | 40 | — |
| CalEssence ® 1500 [8] | — | — | — | 40 |

[5] Precipitated calcium carbonate ex Speciality Minerals Inc., consisting of clustered cubic particles having a calcite crystal habit, a cubic particle shape and a median particle size of 4.5 microns.
[6] Ground calcium carbonate ex Speciality Minerals Inc., having an irregular rhombohedral particle shape and a median particle size of 4 microns.
[7] Precipitated calcium carbonate ex Speciality Minerals Inc., consisting of clustered cubic particles having a calcite crystal habit, a cubic particle shape and a median particle size of 4.5 microns.
[8] Precipitated calcium carbonate ex Speciality Minerals Inc., consisting of semi-regular prismatic particles having a calcite crystal habit, a semi-regular prismatic shape and a median particle size of 12.0 microns.

The PCR and RDA were measured for each of the above formulations and their ratio calculated. PCR was measured using the method of Pickles et al. (*International Dental Journal* 55 (2005), pp. 197-202). RDA was measured using the method for assessment of dentifrice abrasivity recommended by the American Dental Association (Journal of Dental Research 55(4) 563, 1976).

The results are shown in Table 3 below.

| Test Formulation | PCR | RDA | PCR:RDA |
|---|---|---|---|
| Example 1 | 48 | 56 | 0.857 |
| Comparative Example A | 47 | 172 | 0.273 |
| Comparative Example B | 48 | 156 | 0.308 |
| Comparative Example C | 54 | 214 | 0.252 |
| Comparative Example D | 58 | 178 | 0.325 |
| Comparative Example E | 62 | 169 | 0.367 |
| Comparative Example F | 59 | 206 | 0.286 |
| Comparative Example G | 46 | 233 | 0.197 |

The results clearly show the superior performance of Example 1 compared to the Comparative Examples. The cleaning performance of Example 1, as indicated by the PCR measurement, is not significantly inferior to any of the Comparative Examples, but abrasivity, as indicated by the RDA measurement, is greatly reduced.

Example 2 and Comparative Example H

Two oral care formulations were prepared, incorporating different particulate calcium carbonate abrasives. The ingredients of the formulations are shown in Table 4 below. Example 2 represents a formulation according to the invention. The other formulation is a comparative example (not according to the invention).

TABLE 4

| Ingredient | Example 2 | Comp.Ex. H |
|---|---|---|
| Water | to 100 | to 100 |
| Sorbitol (70%) | 31.00 | 31.00 |
| Thickening silica | 7.1 | 7.1 |
| Sodium lauryl sulphate | 1.6 | 1.6 |
| Flavour | 1.2 | 1.2 |
| Sodium monofluorophosphate | 1.09 | 1.09 |
| Trisodium phosphate | 1.07 | 1.07 |
| Titanium dioxide (anatase) | 1 | 1 |
| Sodium carboxymethyl cellulose | 1.0 | 1.0 |
| Sodium saccharin | 0.27 | 0.27 |
| Methyl paraben | 0.15 | 0.15 |
| Propyl paraben | 0.05 | 0.05 |
| Crunchy silica granules | 0.96 | 0.96 |
| Perlite | 0.7 | 0.7 |
| Modified calcium carbonate rods [9] | 41.7 | — |
| Chalk 800M | — | 15 |

[9] Calcium carbonate rods [1], modified by dispersion of the rods into a solution of oleic acid in ethanol, followed by filtering and washing with distilled water to obtain a slurry (36% a.i.).

False teeth (made from PMMA) were embedded in self-setting resins before being brushed by the test formulations, as follows:
Group 1: brushed with clean water only
Group 2: brushed with formulation of Comparative Example H
Group 3: brushed with formulation of Example 2
Group 4: brushed with formulation of Comparative Example H first and then brushed with formulation of Example 2

The brushing medium is made up of the test formulation and water in a weight ratio of 1:2. A brushing machine (Martindale M235), was set up with loading head of 275 g in total. The teeth of Groups 1 to 3 were brushed for 15 minutes at a speed of 150 rpm, and then removed for observation. The teeth of Group 4 were brushed for 15 minutes at a speed of 150 rpm with the formulation of Comparative Example H, then brushed for 15 minutes at a speed of 150 rpm with the formulation of Example 2, and then removed for observation.

Digital images of the brushed teeth were captured by SLR (Canon 550D), and showed gloss differences between the groups. Group 2 teeth showed a lack of luster, indicating surface damage. Group 3 teeth showed higher gloss than group 2 teeth. Group 4 teeth also showed higher gloss than Group 3 teeth.

Figure 1B:
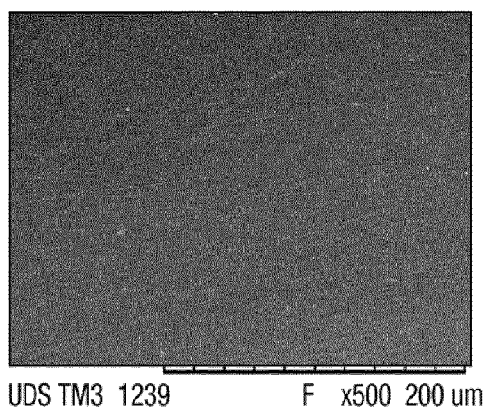
Figure 1C:
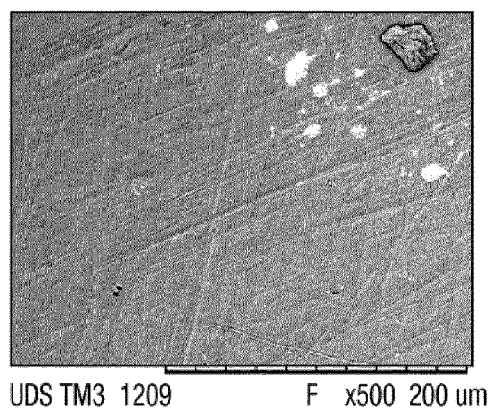
Figure 1D:
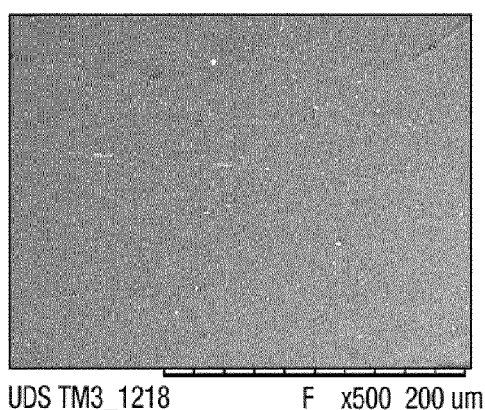
Figure 1E:
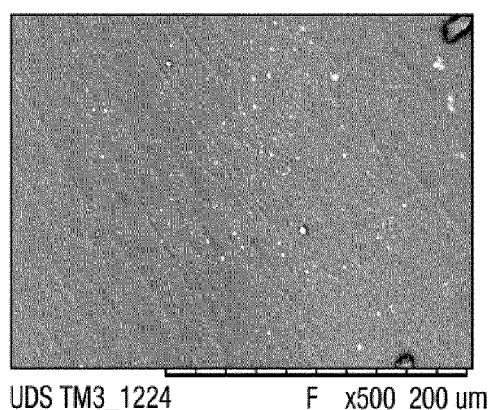

The surface morphologies of the brushed teeth were also observed by Tabletop SEM (Hitachi TM-3000). The results are shown in the appended FIG. 1, and may be summarised as follows:
Image A (Control teeth, no brushing): Surface is very flat without wrinkles.
Image B (Group 1 teeth): Some tiny scratches can be observed.
Image C (Group 2 teeth): Image indicates scratching of the flat denture surface, with some scratches up to several microns.
Image D (Group 3 teeth): Much fewer scratches observed compared to Group 2 teeth, indicating lower damage to the denture surface. Lighter scratches are also observed compared to Group 1 teeth, indicating that the rods lubricate when brushing between toothbrush and surface.
Image E (Group 4 teeth): The number as well as the depth of scratches is less than that observed for the Group 2 teeth, which indicates that the rods have a reparative effect.

The invention claimed is:
1. An oral care composition comprising:
   (a) a continuous phase comprising water or polyhydric alcohol or a mixture thereof; and
   (b) a particulate calcium carbonate abrasive which is a crystalline calcium carbonate in which crystals are acicular with a length ranging from 10 to 30 microns and a width ranging from 0.5 to 1.0 microns; and
   wherein a total weight of the particulate calcium carbonate abrasive ranges from 10 to 70% of a total weight of the composition;
   wherein the oral care composition is configured such that a ratio of a pellicle cleaning ratio (PCR) of the oral care composition to a Radioactive Dentine Abrasion Test (RDA) value of the oral care composition is at least 0.5.

2. The oral care composition according to claim 1, which is in the form of a dentifrice and which further comprises humectant, binder or thickening agent, and surfactant.

3. The oral care composition according to claim 1, wherein the total weight of the particulate calcium carbonate abrasive ranges from 20 to 60% of the total weight of the composition.

4. The oral care composition according to claim 3, which is in the form of a dentifrice and which further comprises humectant, binder or thickening agent, and surfactant.

5. The oral care composition according to claim 1, wherein the total weight of the particulate calcium carbonate abrasive ranges from 30 to 40% of the total weight of the composition.

6. The oral care composition according to claim 5, which is in the form of a dentifrice and which further comprises humectant, binder or thickening agent, and surfactant.

7. The oral care composition according to claim 1, wherein the ratio of PCR of the oral care composition to RDA value of the oral care composition is at least 0.6.

8. The oral care composition according to claim 1, wherein the ratio of PCR of the oral care composition to RDA value of the oral care composition is at least 0.8.

* * * * *